United States Patent [19]
Mansure et al.

[11] Patent Number: 5,827,952
[45] Date of Patent: Oct. 27, 1998

[54] METHOD OF AND APPARATUS FOR DETERMINING DEPOSITION-POINT TEMPERATURE

[75] Inventors: Arthur J. Mansure; James J. Spates; Stephen J. Martin, all of Albuquerque, N. Mex.

[73] Assignee: Sandia National Laboratories, Albuquerque, N. Mex.

[21] Appl. No.: 863,936

[22] Filed: May 27, 1997

Related U.S. Application Data

[63] Continuation-in-part of Ser. No. 621,929, Mar. 26, 1996, Pat. No. 5,661,233.

[51] Int. Cl.$^6$ .......................... G01N 11/00; G01N 27/00; C10G 43/08
[52] U.S. Cl. .......................... 73/61.45; 73/61.62; 73/590; 73/61.49; 374/16; 374/54; 208/37
[58] Field of Search .................. 73/61.45, 54.16, 73/54.41, 54.42, 61.49, 61.62; 374/16, 17, 20, 45; 356/70; 166/250

[56] References Cited

U.S. PATENT DOCUMENTS

| | | | |
|---|---|---|---|
| 3,623,363 | 11/1971 | Dory | 73/194 A |
| 3,643,492 | 2/1972 | Simpson | 73/17 A |
| 3,677,064 | 7/1972 | Simpson | 73/17 R |
| 3,840,352 | 10/1974 | Scheffel | 44/62 |

(List continued on next page.)

OTHER PUBLICATIONS

James N. Howell and F. W. Jessen, "Determination of the Viscosity–Temperature Relationship for Crude Oils with the Ultra–Visconson," *Journal of Petroleum Technology*, vol. 8, pp. 95–97, Sep., 1956.

V. R. Kruka, E. R. Cadena, and T. E. Long, "Cloud–Point Determination of Crude Oils," *Journal of Petroleum Technology*, vol. 47, pp. 681–687, Aug. 1995.

James J. Spates, Stephen J. Martin, Arthur J. Mansure, and Jeffrey W. Germer, "Cloud Point Determination Using a Thickness Shear Mode Resonator," presented at the 210th Chemical Society National Meeting and Exposition, Chicago, IL, Aug. 20–24, 1995.

"ASTM Standard D 2500: Standard Test Method for Cloud Point of Petroleum Products," *Annual Book of ASTM Standards* (American Society for Testing and Materials, Philadelphia, PA), Dec. 1991.

Kurt O. Wessendorf, "The Level Oscillator for Use in High Resistance Resonator Applications," presented at the 1993 IEEE International Frequency Control Symposium, Albuquerque, NM, Jul., 1993.

K. M. Barker, "Formation Damage Related to Hot Oiling" presented at the SPE Production Operations Symposium, held in Oklahoma City, OK, Mar. 8–10, 1987.

A. J. Mansure and K. M. Barker, Practical Hot Oiling and Hot Watering for Paraffin Control, held at the SPE Production Operations Symposium, in Oklahoma City, OK, Mar. 21–23 1993.

*Primary Examiner*—Hezron E. Williams
*Assistant Examiner*—J. David Wiggins

[57] ABSTRACT

Acoustic-wave sensor apparatus and method for analyzing a normally liquid petroleum-based composition for monitoring deposition-point temperature. The apparatus includes at least one acoustic-wave device such as SAW, QCM, FPM, TSM or APM type devices in contact with the petroleum-based composition for sensing or detecting the surface temperature at which deposition occurs and/or rate of deposition as a function of temperature by sensing an accompanying change in frequency, phase shift, damping voltage or damping current of an electrical oscillator to a known calibrated condition. The acoustic wave device is actively cooled to monitor the deposition of constituents such as paraffins by determining the point at which solids from the liquid composition begin to form on the acoustic wave device. The acoustic wave device can be heated to melt or boil off the deposits to reset the monitor and the process can be repeated.

34 Claims, 4 Drawing Sheets

U.S. PATENT DOCUMENTS

| | | | |
|---|---|---|---|
| 4,115,245 | 9/1978 | Harrison et al. | 208/33 |
| 4,519,717 | 5/1985 | Jones | 374/17 |
| 4,804,274 | 2/1989 | Green | 374/17 |
| 4,925,314 | 5/1990 | Claudy | 374/16 |
| 5,007,733 | 4/1991 | Laurent | 356/70 |
| 5,088,833 | 2/1992 | Tsang | 374/17 |
| 5,201,215 | 4/1993 | Granstaff | 73/54.41 |
| 5,283,037 | 2/1994 | Baer et al. | 422/82.01 |
| 5,306,644 | 4/1994 | Myerholtz et al. | 436/149 |
| 5,416,448 | 5/1995 | Wessendorf | 331/116 R |
| 5,452,232 | 9/1995 | Espinosa | 364/498 |
| 5,475,612 | 12/1995 | Espinosa | 364/500 |
| 5,616,856 | 4/1997 | Castel | 73/61.45 |
| 5,661,233 | 8/1997 | Spates et al. | |

METHOD OF AND APPARATUS FOR DETERMINING DEPOSITION-POINT TEMPERATURE

CROSS-REFERENCE TO RELATED APPLICATIONS

This patent application is a continuation-in-part to Martin et al., U.S. Ser. No. 08/621,929, "Acoustic-Wave Sensor Apparatus for Analyzing a Petroleum-Based Composition and Sensing Solidification of Constituents Therein," filed on Mar. 26, 1996, now U.S. Pat. No. 5,661,233 dated Aug. 26, 1997.

GOVERNMENT RIGHTS

This invention was made with United States Government support under Contract No. DE-AC04-94AL85000 awarded by the U.S. Department of Energy. The Government has certain rights in this invention.

BACKGROUND OF THE INVENTION

The present invention relates generally to the field of acoustic-wave devices or sensors. More specifically, the present invention relates generally to an acoustic-wave sensor apparatus and method for analyzing fluids, such as petroleum or petroleum-based compositions (e.g., crude oil, hydrocarbons), to determine the deposition-point temperature thereof. In addition, the present invention provides a means for measuring the rate of deposition as a function of temperature. Deposition is a major problem, for example, in the transportation of petroleum-based compositions by pipelines.

Many petroleum-based fluids are a complex mixture of components including components that are normally solids at ambient temperature conditions (e.g., wax in crude oil). Petroleum-based compositions (e.g., crude oil and hydrocarbon compositions formed therefrom) can contain substantial amounts of petroleum waxes, or paraffins, and asphaltenes. Paraffins are solid, crystalline hydrocarbon mixtures derived from the paraffin, distillate portion of crude petroleum. Paraffins are defined herein as any alkanes having the generic formula $C_nH_{2n+2}$, and are used in particular to refer to higher molecular weight alkane components of petroleum-based compositions with a chain length greater than about $C_{20}$, and typically in the range of about $C_{20}$ to $C_{50}$. Asphaltenes are any of the dark, solid constituents of crude oils and other bitumens which are soluble in carbon disulfide but insoluble in paraffin naphthas; they hold most of the organic constituents of bitumens aliphatic solvents.

When such a normally liquid petroleum-based composition is cooled below a certain temperature, referred to herein as a cloud-point temperature solid particles or crystals form in suspension. Cloud-point temperature is that temperature at which the dissolved components become supersaturated and suspended crystals occur (contains more solute than is needed to cause saturation). These solidified constituents (having a soft or semi-rigid structure) can then deposit (or crystallize) below a certain temperature referred to herein as a deposition-point temperature on an inner surface of a pipeline resulting in a narrowing of the pipeline and restricting transport of the petroleum-based composition (e.g., crude oil during some stage of recovery, storage, transport, or refining). The deposition-point temperature is usually essentially the same as the cloud-point temperature or just below it, however, the two temperatures may be different. The deposition-point temperature occurs when the temperature drops below the point where the crystals in the fluid become too heavy to remain in suspension or they have sufficient chemical adhesion to stick to surfaces. Additionally, these solidified constituents can accumulate on an inner surface of a storage tank leading to a variable temperature-dependent concentration of constituents dissolved within the petroleum-based composition. This can be disadvantageous because the accumulated constituents can later be dissolved back into the petroleum-based composition at a high concentration when the ambient temperature exceeds the cloud-point temperature. Furthermore, the presence of dissolved constituents can limit a temperature range for usage of the petroleum-based composition (e.g., fuels such as diesel oil or gasoline, lubricants, or process feedstocks) requiring a measurement of the cloud-point temperature or deposition-point temperature and some means for removing the dissolved and deposited constituents, at least in part, to reduce the cloud-point and deposition-point temperature below a predetermined level.

Conventional techniques for determining deposition-point temperature are either indirect (e.g., cloud point) or subjective (depend upon when the operator visually notices deposition). Additionally, conventional systems are not easily automated, and thus, not useful for process monitoring/control. Furthermore, conventional systems require large amounts of fluid to contain enough material to lay down significant deposits. Conventional systems are not very sensitive.

Conventional techniques for determining deposition-point temperature include use of a probe such as a cold finger, an internally-cooled probe, or a tube immersed in the fluid. To determine if deposition has occurred, the probe is periodically removed from the fluid and visually inspected for deposits. If, after sufficient time, no deposition has occurred, the temperature is lowered and the process repeated to determine if deposition has occurred. An indirect method of determining the deposition point is to determine the cloud-point temperature of the fluid itself and assume the deposition point is the same as the cloud point.

Some methods for determining the cloud point for crude oils have been reviewed in an article entitled "Cloud-Point Determination for Crude Oils" by V. R. Kruka et al. (*Journal of Petroleum Technology*, vol. 47, pp. 681–687, August 1995) which is incorporated herein by reference. Briefly, these methods are based primarily on visual observations, light transmission or scattering measurements, heat capacity and thermal conductivity measurements, density variation measurements, and viscosity measurements.

An American Society for Testing and Materials (ASTM) standard test method based on visual observations is also disclosed in ASTM Standard D-2500 (Standard Test Method for Cloud Point of Petroleum Oils, pp. 199–20 1, ASTM, 199 1). This visual observation method is limited to a relatively transparent oil sample; and it is based on an operator's subjective judgment of a temperature at which wax particles begin to appear in the oil sample, which is variable from one sample to the next and open to error. More objective cloud-point temperature measurements are possible with light-transmission or light-scattering measurements; but these measurements generally require a relatively transparent oil sample.

Viscosity cloud-point measurements have been based on measuring the energy required to produce sliding motion in a thin alloy steel blade by magnetostrictive excitation (see J. F. Nowell et al., *Journal of Petroleum Technology*, vol. 8, pp. 95–97, September 1956); or alternately on falling balls or rotating viscometers.

Numerous patents have also issued for determining the cloud point of oil and petroleum products, based on methods similar to those listed in the review article of Kruka et al. (see U.S. Pat. Nos. 3,580,047; 3,643,492; 3,677,064; 4,519, 717; 4,804,274; 4,925,314; 5,007,733; and 5,088,833). Thus, a simple and reliable apparatus and method is needed for analyzing petroleum-based compositions and for sensing the deposition of constituents therein. The apparatus and method should be able to distinguish between suspension and deposition. Such analysis can provide information about a deposition-point temperature below which some of the constituents (e.g., paraffins) begin to solidify or crystallize and form deposits, can provide information about a cloud-point temperature below which some of the constituents (e.g., paraffins) begin to solidify or crystallize (see below), a pour-point temperature below which the petroleum-based composition congeals and does not readily pour or flow, and/or a freeze-point temperature at which the petroleum-based composition entirely solidifies.

The apparatus and method of the present invention, which teaches an acoustic-wave device or sensor, can be used to analyze petroleum-based compositions having a wide range of viscosities and to provide information about a deposition point or a cloud point. The acoustic-wave sensor apparatus and method of the present invention can be applied to analyze petroleum-based compositions in many different forms and at many different stages of oil recovery, transport, storage, processing or use, including in the form a small-volume (e.g., about 25 $cm^3$) sample placed within a container; in the form of a composition flowing through a pipeline during recovery, transport, or processing; or in the form of a composition contained within a tank for storage or use. The apparatus and method of the present invention can be used to provide indications of a solidification of constituents within a pipeline or storage tank and of an accumulation or deposition of the solidified constituents on an inner surface of the pipeline or storage tank where the temperature is not actively controlled. Additionally, the apparatus of the present invention can be used to provide information as the rate and amount of deposition to determine when the solidified constituents accumulate sufficiently to create problems. Additionally, the present invention is that the acoustic-wave sensor apparatus can be operatively connected to means for maintaining the petroleum-based composition above a predetermined point such as a deposition point, cloud point, a pour point, or a freeze point. Furthermore, the apparatus and method of the present invention provides a high-measurement sensitivity, thereby allowing the determination of a plurality of cloud or deposition points within a petroleum-based composition due to different constituents which solidify at different temperatures.

BRIEF SUMMARY OF THE INVENTION

An acoustic-wave sensor apparatus and method are provided for analyzing a fluid having constituents which form deposits on the sensor when the sensor is cooled below a deposition-point temperature. The apparatus comprises an acoustic-wave device or sensor having a crystal, the crystal having at least one surface in contact with the fluid for detecting the presence of solidified constituents accumulated thereon and generating an output signal in response to the accumulation. The acoustic-wave sensor apparatus comprises a piezoelectric acoustic-wave device such as a thickness-shear-mode (TSM) device (also termed a quartz crystal microbalance), a surface-acoustic-wave (SAW) device, an acoustic-plate-mode (APM) device, or a flexural-plate-wave (FPW) device; and further comprises an electrical circuit for activating the acoustic-wave device to generate the output signal therefrom. The acoustic-wave sensor apparatus can also include temperature sensing means in thermal contact with the fluid for measuring the temperature thereof, and means for varying the temperature of the crystal over a predetermined temperature range including the deposition-point temperature. The apparatus includes a means for controlling the temperature of the acoustic wave sensor to be either cooler or hotter than the temperature of the fluid being analyzed. This temperature control means can be either a separate device that is thermally connected to the acoustic wave sensor, such as a thermoelectric cooler coupled to the crystal by a heat transfer fluid, or it can be incorporated into the acoustic wave device by including a Peltier junction into the acoustic wave device.

Embodiments of the present invention can be used for analyzing a sample of a fluid placed within a container to determine information including a deposition point or a cloud point. Other embodiments of the present invention can be used for analyzing a fluid contained within a pipeline or storage tank, with the output signal from the acoustic-wave device providing information about solidification of constituents on an inner surface of the pipeline or storage tank; or about the attainment of a deposition point; cloud point, a pour point, or a freeze point of the fluid. Yet other embodiments of the present invention can provide an output that is operatively connected to means for maintaining the fluid at a predetermined point such as the deposition point, the cloud point, the pour point, or the freeze point during recovery, transport, processing, storage or use of the fluid, and during other applications.

The novel features of the present invention will become apparent to those of skill in the art upon examination of the following detailed description of the invention or can be learned by practice of the present invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

BRIEF DESCRIPTION OF THE DRAWINGS

The accompanying figures, in which like reference numerals refer to identical or functionally similar elements throughout the separate views and which are incorporated in and form part of the specification, further illustrate the present invention and, together with the detailed description of the invention, serve to explain the principles of the present invention.

DETAILED DESCRIPTION OF THE INVENTION

Figure 1:
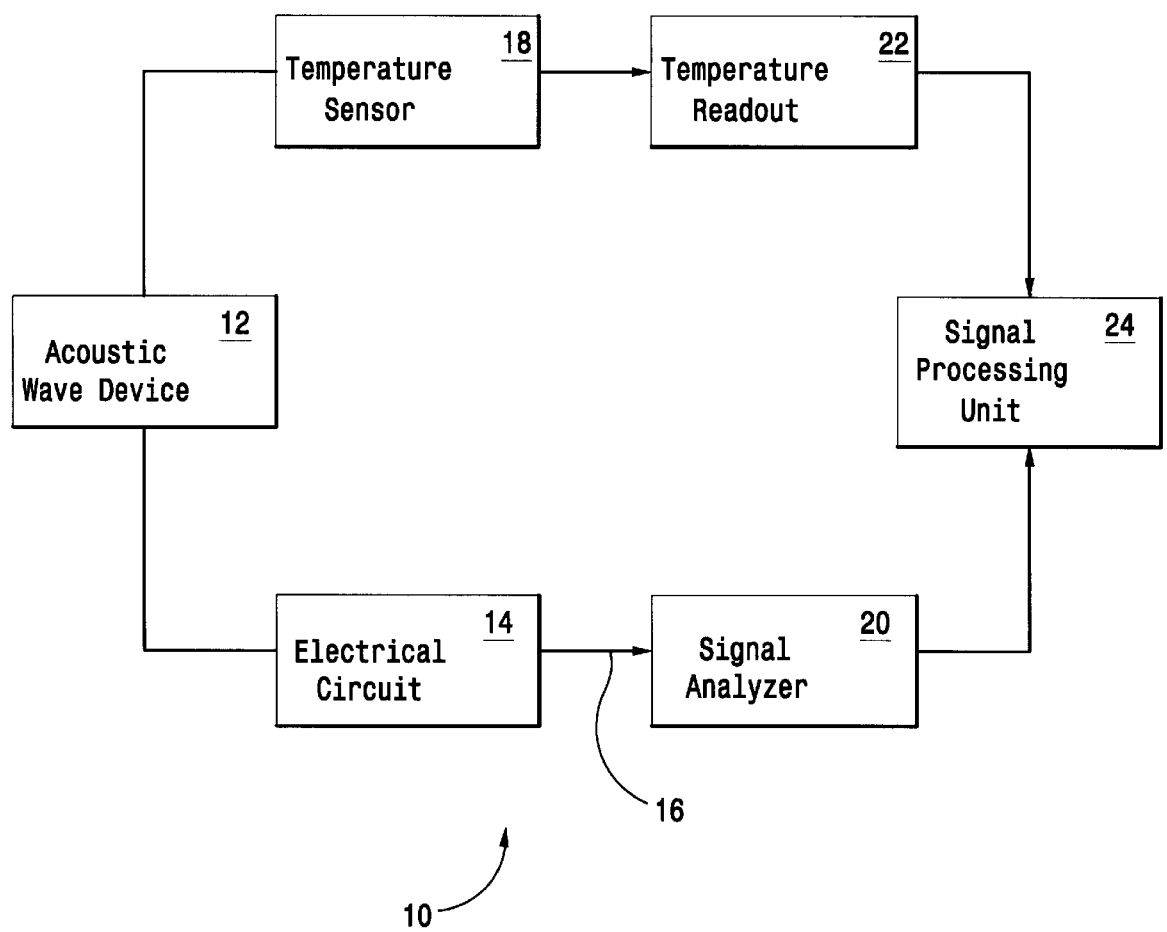
FIG. 1 shows a block diagram of an embodiment of an acoustic-wave sensor apparatus according to the present invention.

The method and apparatus of the present invention can be used to monitor/control deposition-point temperature and determine deposition rate of constituents such as paraffins and asphaltenes in a normally-liquid petroleum-based composition using an acoustic-wave sensor apparatus 10. Acoustic-wave sensor apparatus 10 can be a thickness-shear-mode (TSM) device (also termed a quartz crystal microbalance), a surface acoustic-wave device, an acoustic-plate-mode device, a flexural-plate-wave device, or a similar device.

The present invention provides a means for both cooling and heating crystal plate 26 (shown in FIG. 3) of acoustic-wave device 12. By actively cooling crystal plate 26 below the deposition-point temperature of composition 100, the deposition of solids on crystal plate 26 can be monitored and controlled. By heating crystal plate 26, the deposits of solidified constituents on crystal plate 26 can be melted or boiled off, thus resetting acoustic-wave sensor apparatus 10 (to a known condition) or allowing deposits that dissolve to be differentiated from deposits that do not dissolve as the temperature rises. Means such as a thermoelectric cooler 230 (shown in FIG. 3) or the like may be provided proximate to acoustic-wave device 12 for periodically removing the accumulation of solidified constituents from acoustic-wave device 12. This can also be used to determine the degree by which the fluid (composition 100) stream temperature must be raised to prevent deposition in a process stream having a temperature that is currently cooler than the deposition-point temperature of composition 100. Additionally, the deposition monitor of the present invention can also be used to determine the amount and type of chemical additives (e.g., a solvent, a dispersant, a surfactant, a crystal modifier, combinations thereof, etc.) needed for controlling deposition in composition 100 stream. Additionally, the heating and cooling means combine to provide a means whereby the rate of deposition of constituents in composition 100 can be measured as a function of the temperature difference between crystal plate 26 and composition 100 being monitored.

The particular values and configurations discussed in the following exemplary embodiments can be varied and are cited merely to illustrate certain embodiments of the present invention and are not intended to limit the scope of the invention. Referring to FIG. 1, there is shown a block diagram of a non-limiting example of an acoustic-wave sensor apparatus 10 according to the present invention. Apparatus 10 is useful for analyzing a petroleum-based composition 100 (see FIG. 3) contacting apparatus 10 to sense any deposition of constituents within composition 100. Acoustic-wave sensor apparatus 10 comprises at least one acoustic-wave device 12 connected to an electrical circuit 14 for activation or excitation thereof and for generating an output signal 16 from acoustic-wave device 12 that is responsive to an accumulation of deposits on at least one surface of acoustic-wave device 12. The sensor portion of apparatus 10 can be used as a retrofitted device for attaching the sensor portion of apparatus 10 to a pipeline, storage tank, sample container, or the like that contains the petroleum-based composition to be analyzed as exemplarily shown in FIG. 3.

Figure 2:
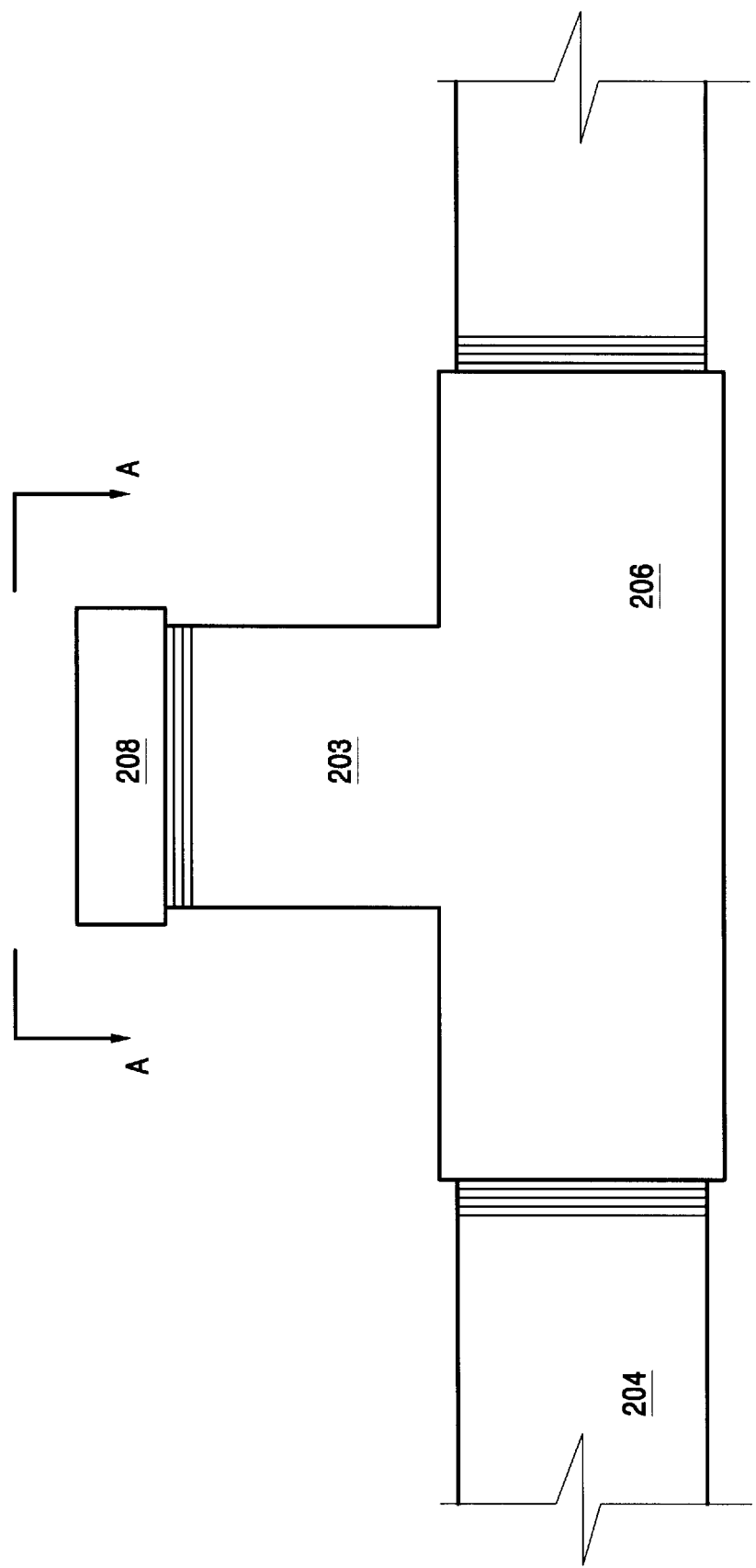
FIG. 2 shows a side view of a pipe with a pipeline tee in which a second embodiment of the present invention can be mounted for deposition monitoring.
Figure 3:
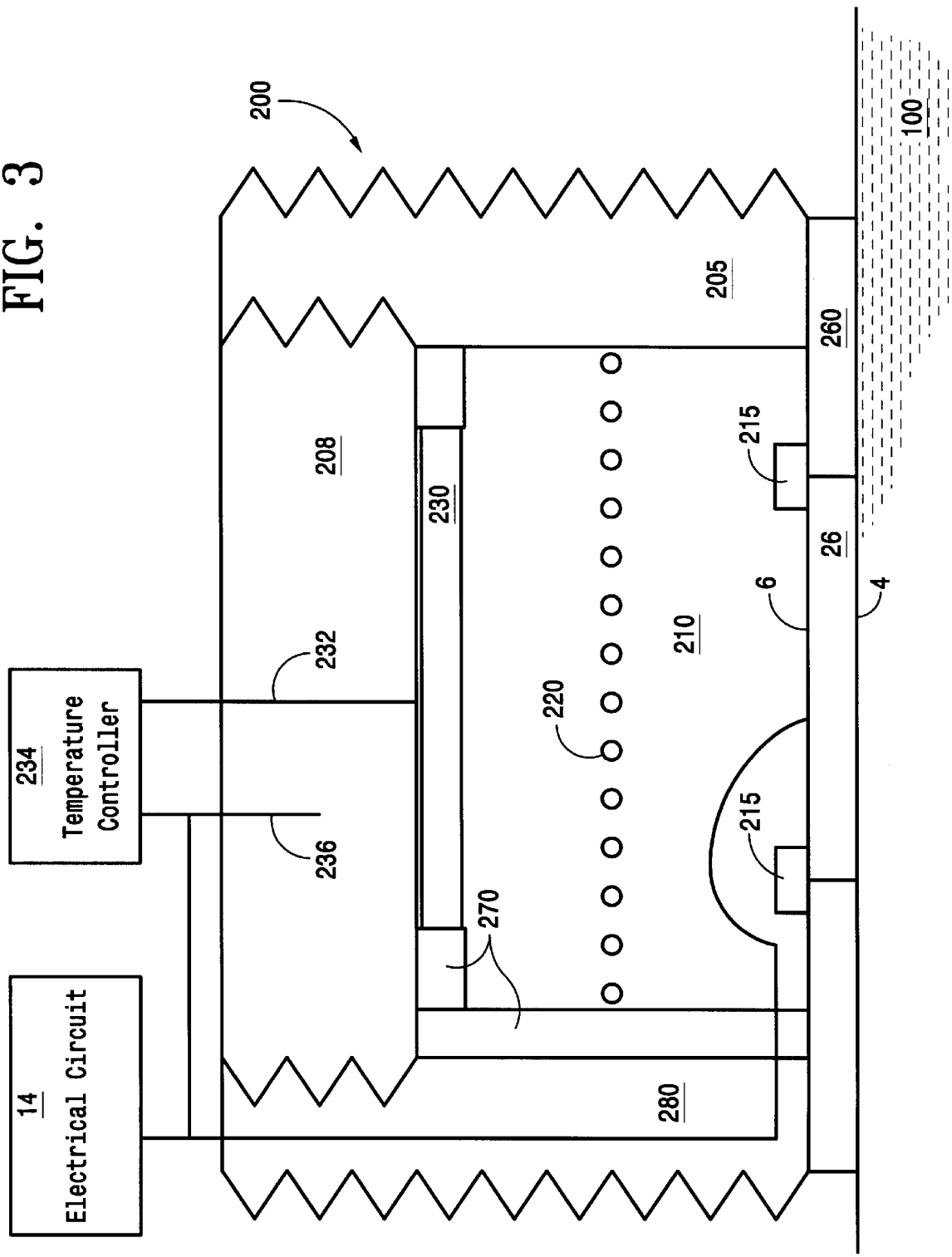
FIG. 3 shows a cross-sectional view (taken along view lines A—A in FIG. 2) of the second embodiment of the acoustic-wave sensor apparatus mounted within a pipeline tee with the crystal surface mounted flush to the fluid direction flow within the pipeline (only one side of the crystal is allowed to be in contact with the fluid) according to the present invention.

Referring to FIG. 3, apparatus 12 can be flush mounted to the fluid direction flow of composition 100 within a pipe or pipeline tee 206 (a section with a side arm 203 perpendicular to the pipe 204 as shown in FIG. 2) to monitor the deposition-point temperature of composition 100. A pipe plug screws into or mates with the tee or coupling. An exposed side 4 of crystal plate 26 of a TSM resonating quartz crystal can be placed in contact with fluid composition 100 (see FIG. 3) being examined while an isolated side 6 (opposite of exposed side 4) of the crystal surface 26 (plate 26) is cooled (or vice versa) and isolated from composition 100 (only one of the sides 4 or 6 is exposed to composition 100). Thus, the surface temperature of crystal plate 26 is depressed below the temperature of composition 100 to monitor the deposition-point temperature. Deposition-point temperature is determined by measuring the change in resonant frequency, delta f, and/or damping voltage, delta V, when deposition occurs on the surface (exposed side 4) of crystal plate 26. Deposition occurs when the surface temperature of exposed side 4 (or whichever surface is in contact with composition 100) drops below the point where dissolved constituents in composition 100 become supersaturated and are no longer held in suspension. By analyzing the output signals of the crystal plate 26 (through crystal feedthrough 280) as a function of time and temperature difference, the rate of deposition can be measured-as a function of temperature difference between the surface of crystal plate 26 and composition 100.

Acoustic-wave sensor apparatus 10 of the present invention can further include a temperature sensor 18 connected to the acoustic-wave device 12 as shown in FIG. 1 for sensing the temperature of the surface of crystal plate 26 that is in contact with composition 100. The acoustic-wave sensor apparatus 10 can further include elements such as a signal analyzer 20, a temperature readout 22 and a signal processing unit 24 for display and analysis of signals output from the apparatus 10 as shown in FIG. 1. These display and analysis elements can either be provided by a user of apparatus 10; or else they can be incorporated, at least in part, into electrical circuit 14. The acoustic-wave device 12 can be a thickness-shear-mode (TSM) device (also termed a quartz crystal microbalance or QCM). However, for other embodiments of the present invention, acoustic-wave device 12 can be any other type of piezoelectric acoustic-wave device as known to the art, including a surface-acoustic-wave (SAW) device, an acoustic-plate-mode (APM) device or a flexural-plate-wave (FPW) device.

Figure 4:
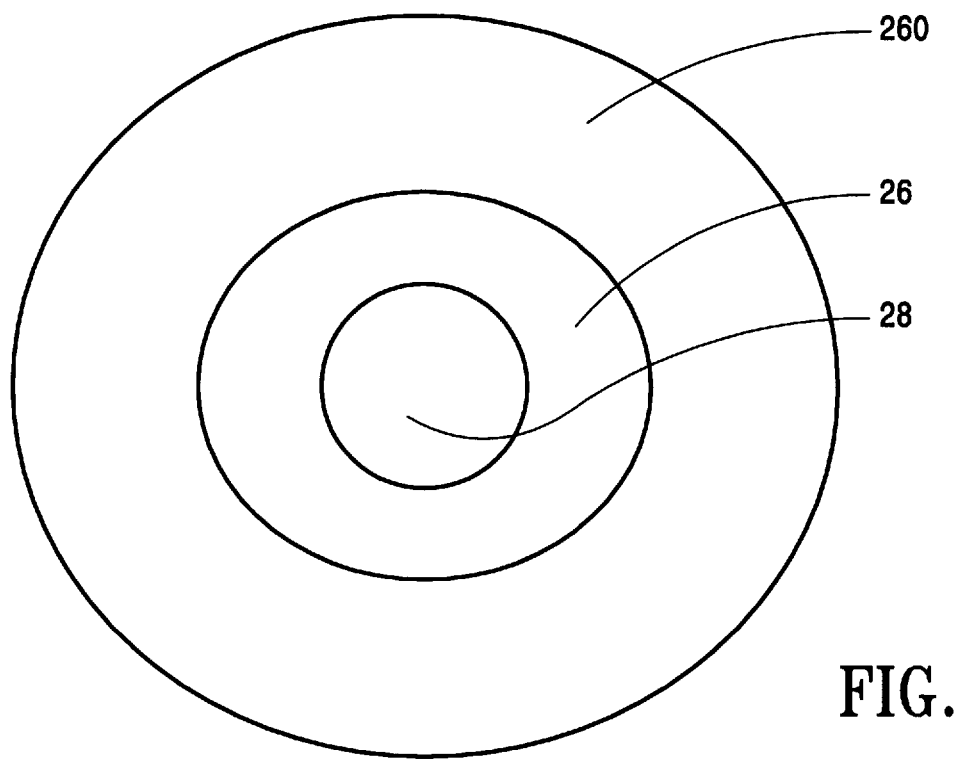
FIG. 4 shows a plan view of the second embodiment when viewed from exposed side 4 (looking up into exposed side 4 of FIG. 3) apparatus according to the present invention.

In FIG. 1, acoustic-wave device 12, in the form of a TSM device, comprises a thin wafer or (highly-polished) crystal plate 26 of a piezoelectric material such as an AT-cut quartz crystal with electrodes 28 (shown in FIG. 4) formed on opposite sides of the plate 26. Applying a radio-frequency (rf) electrical signal to electrodes 28 causes the piezoelectric material to be excited into a shear mode of vibration in which the faces of plate 26 undergo in-plane displacement. Because of the piezoelectric properties and crystalline orientation of the AT-cut quartz crystal plate 26, the application of a voltage between electrodes 28 results in a shear deformation of crystal plate 26 that excites a resonance therein when the applied voltage has an excitation frequency with an acoustic wavelength approximately equal to an odd sub-multiple of the thickness of crystal plate 26. At these resonant frequencies, a standing acoustic shear wave is generated across the thickness of crystal plate 26 for the fundamental and higher harmonic resonances. These resonant frequencies can also be altered or shifted by the presence of a material (e.g., the solidified constituents of the petroleum-based composition) accumulated on one or more exposed sides of acoustic-wave device 12, thereby providing a means for sensing solidified constituents (deposits) within petroleum-based composition 100.

U.S. Pat. No. 5,201,215, which is incorporated herein by reference, to Granstaff et al. discloses details of a quartz crystal microbalance (QCM) or TSM device. Granstaff et al. consider the case of a QCM loaded from above by a surface mass layer and a contacting fluid, with the mass layer being a solid such as a metal layer rigidly attached to the QCM. Granstaff teaches that any solid on a surface of an acoustic-wave device must be rigidly adhered thereto. Although many features of Granstaff et al. are applicable to the present invention, the present invention is different from Granstaff et al. in teaching operation of TSM acoustic-wave device 12 in contact with a viscous (i.e., greater than or equal to about 10 centipoises (cP) viscosity) petroleum-based composition (e.g., a hydrocarbon composition) to measure solidified constituents accumulated on a surface of acoustic-wave device 12—but not rigidly adhered thereto—with the solidified constituents further comprising a paraffin or asphaltene which is characterized by a soft or semi-rigid structure (as opposed to Granstaff et al. patent, which teaches a mass layer in the form of a metal that is solid and rigidly attached to the QCM). Furthermore, the present invention teaches how to control the temperatures of composition 100 and crystal plate 26 so as to control the deposition process, thereby, qualitative and quantitative measurements of deposition to be made and, thereby, differentiate paraffin from other deposits. U.S. patent application Ser. No. 08/108,397 to Martin et al. (Aug. 18, 1993 filing date) discloses usage of an acoustic-wave device for an in-situ measurement of the density and viscosity of working fluids such as oil in an operating engine, and is also incorporated herein by reference. U.S. Ser. No. 08/108,397 generally teaches that oscillation of an acoustic wave device ceases for use with a fluid having a viscosity of more than about 10 centipoises (see FIG. 11 of U.S. patent application Ser. No. 08/108,397). However, the teaching of the present invention is that acoustic-wave device 12 can be used for measurements within a fluid (e.g., a hydrocarbon composition) having a viscosity greater than about 10 centipoises if an improved electrical circuit 14 is used for activating acoustic-wave device 12.

Acoustic-wave device 12 can be, for example, a 2.54 cm diameter, synthetic AT-cut quartz crystal plate 26. Those skilled in the art will know that other sizes, shapes, and crystalline cuts of quartz, as well as lithium niobate, and certain cuts of lithium tantalate, or any piezoelectric material that allows shear deformations to be electrically excited can be used for forming acoustic-wave device 12.

Quartz crystal plate 26 in the example of FIG. 1 can be about 0.33 millimeters thick, with smooth side surfaces that have been lapped and polished. Electrodes 28 can be deposited and patterned on exposed side 4 and isolated side 6 of crystal plate 26 by means known to the art including vacuum-deposition of an adhesion layer (e.g., about 1 to 20 manometers or more of chromium or titanium), followed by deposition of a thin layer (e.g., about 100 to 200 nanometers) of gold or any other conductive metal.

Each of the electrodes 28 can have a generally circular shape (e.g., about 0.5–1.5 cm in diameter) centered on a surface of crystal plate 26 (see FIG. 4), with a contact pad portion extending outward along the surface of the crystal plate 26 for providing an electrical connection to each electrode 28 for activating acoustic-wave device 12. Electrodes 28 can have different diameters, with one of the electrodes 28 generally serving as a ground electrode; and the other electrode 28 generally serving as a radio-frequency (rf) electrode for applying a rf electrical signal (i.e., a rf voltage) and generating an oscillating electric field across the thickness of crystal plate 26 to excite an acoustic vibration mode therein. A coaxial cable or stripline can be used to provide an electrical connection between acoustic-wave device 12 and electrical circuit 14 for activating acoustic-wave device 12.

Referring to FIG. 3, electrical circuit 10 can be provided proximate to acoustic-wave device 12 within a housing (e.g., a plug or fitting attached or screwed into a pipe tee or attached to the pipe so that the face of the plug or fitting is perpendicular to the composition flow. The plug or fitting can be adapted for applications, for example, to enhance the performance of the acoustic-wave sensing means (e.g., to implement a change in pipe diameter so as to control the fluid velocity across the exposed surface of the crystal plate.)) and electrically connected thereto for providing the rf voltage across electrodes 28 to activate acoustic-wave device 12. Electrical circuit 10 can include any type of oscillator circuit as known to the art for activating or exciting acoustic-wave devices. The electrical circuit can be a lever oscillator circuit similar in design and function to one of the circuits disclosed in U.S. Pat. No. 5,416,448 to Wessendorf, which is incorporated herein by reference (see also K. O. Wessendorf, "The Lever Oscillator for use in High Resistance Resonator Applications," IEEE International Frequency Control Symposium, pp. 711–717 (1993).). The temperature of crystal plate 26 is controlled by circuitry that senses the ambient temperature and crystal plate 26 temperature and adjusts the power to thermoelectric cooler 230 accordingly. The use of a lever oscillator circuit is particularly advantageous for allowing operation of acoustic-wave device 12 over a wide range of resonator resistance due to damping which occurs when at least one surface of acoustic-wave device 12 is in contact with composition 100. Although the patent of Wessendorf discloses use of lever oscillator circuits with liquids having viscosities up to about 10 centipoises, we have discovered that such circuits may be adapted for use with a viscosity greater than 10 centipoises as is characteristic of many different petroleum-based hydrocarbon compositions 100, including crude oil and products refined therefrom (e.g., fuel oils, lubricants, gasoline, solvents etc.). (It should be noted that cooling of composition 100 produces solidified constituents therein that produce a slurry, which further increases the viscosity of composition 100 beyond 10 centipoise.)

Acoustic-wave device 12 can be used as a frequency-control element of the lever oscillator circuit (i.e., electrical circuit 14), with the lever oscillator circuit both tracking a frequency of oscillation (i.e., a resonant frequency) of acoustic-wave device 12 and providing a feedback or damping voltage or current to maintain an amplitude of oscillation of acoustic-wave device 12 at a substantially constant level (not shown). In this way, the lever oscillator circuit can compensate for changes in damping of acoustic-wave device 12 due both to changes in the viscosity of composition 100 and also to an accumulation of solidified constituents from composition 100 on the exposed surface 4 of crystal plate 26 of acoustic-wave device 12 (e.g., due to solidified constituents forming therein at a temperature at or below the deposition-point temperature characteristic of a particular composition 100). Because both of these factors that change the viscosity of composition 100 can occur at or below a deposition point thereof, one or both of the frequency of oscillation (or a shift thereto) and the damping voltage or current (or a shift thereof) can provide an indicator of the deposition point.

The deposition point of composition 100 is defined herein as a particular point, usually defined in terms of a deposition-point temperature, at which some of the constituents of the petroleum-based composition such as paraffins first begin to precipitate, solidify or crystallize and deposit as the petroleum-based composition is cooled at a predetermined rate, generally in a range of about 0.2 to 2° C./minute. If cooling of exposed surface 4 of crystal plate26 is continued, composition 100 often possesses a viscosity at which it will not flow. The temperature at which this occurs under certain conditions is termed a freeze-point temperature or a solid-point temperature, with a pour-point temperature further being defined as a temperature about 3° C. above the freeze-point temperature. The deposition point is characterized by the change in resonant frequency, delta f, and/or damping voltage, delta V, when deposition occurs. The cloud point is characterized by a rapid change in optical characteristics of the petroleum-based composition 100 which becomes cloudy or hazy at the cloud point due to constituents therein beginning to solidify or crystallize. Thus, the cloud-point temperature for a particular type of composition 100 can provide an indication of the amount of paraffin or petroleum wax therein, which in turn can affect a quality (e.g., determined at least in part by a useful temperature range for use of the composition) and a market value of the petroleum-based composition.

Although the deposition point generally refers to the point at which constituents of composition 100 first begin to crystallize and deposit, it will be understood that many types of petroleum-based compositions such as crude oil have a complex chemical structure, comprising a plurality of different chemical compounds or constituents, with each constituent having different characteristics including a different temperature at which it begins to deposit. Thus, a sensitive enough instrument such as acoustic-wave sensor apparatus 10 of the present invention can allow the determination of multiple points at which different constituents of a particular petroleum-based composition begin to deposit, thereby providing additional information about the petroleum-based composition. The acoustic-wave device of the present invention is at least an order of magnitude more sensitive than conventional systems.

Additionally, electrical circuit 14 can be an instrument such as a network analyzer, a frequency-sweep oscillator or the like for measuring a frequency-response characteristic of acoustic-wave device 12 near a resonant frequency thereof so that one or more electrical characteristics (e.g., capacitance, reactance, and resistance) of acoustic-wave device 12 can be determined by fitting the frequency response characteristic to an equivalent-circuit model of acoustic-wave device 12. The use of a network analyzer and a frequency-sweep oscillator for characterizing an acoustic-wave device is disclosed in the Granstaff et al. patent (U.S. Pat. No. 5,201,215), which is incorporated herein by reference. By fitting the measured electrical characteristics of acoustic-wave device 12 to an equivalent circuit model, the accumulation of solidified constituents on at least one surface of acoustic-wave device 12 and a density viscosity product of the petroleum-based composition in contact with acoustic-wave device 12 can be determined.

Electrical circuit 14 provides an output signal 16 in response to the accumulation of solidified constituents on the exposed surface 4 of acoustic-wave device 12. Output signal 16 indicates one or more parameters of acoustic-wave device 12, depending on the particular type of acoustic-wave device 12 used for practice of the present invention, that can be a frequency of oscillation, a feedback or damping voltage or current, or a combination thereof. A calibration of acoustic-wave device 12 can be performed by contacting one or more surfaces of acoustic-wave device 12 with petroleum-based composition 100 and measuring an unperturbed value of one or more parameters of acoustic-wave device 12 in the absence of any solidified constituents. Alternately, acoustic-wave device 12 can be calibrated prior to any contact with petroleum-based composition 100. With a subsequent cooling of the surface of crystal plate 26 to produce deposited constituents thereon, each parameter of acoustic wave device 12 can then be measured as a deviation or shift from its unperturbed value (e.g., a shift in the frequency of oscillation; a shift in the damping voltage; or both).

Referring to FIG. 1, output signal 16 is processed with, for example, a signal analyzer 20 (e.g., a frequency counter, a voltmeter, an analog-to-digital converter, or the like) which can be connected to a signal processing unit 24 such as a computer or the like for analysis, data acquisition, data display, or for providing an output for closed-loop feedback control. The signal processing unit 24 can further receive an input from a temperature readout 22 connected to temperature sensor 18 to provide information about the temperature of the surface of crystal plate 26 for correlation with information generated by acoustic-wave device 12 to determine a deposition point of composition 100.

A measurement of the frequency of oscillation (or a shift thereof) alone in some instances does not provide unique information about a thickness of an accumulation of solidified constituents on the surface(s) of acoustic-wave device 12. This is due to a compliant film (e.g., the solidified constituents comprising paraffin being accumulated on a surface of acoustic-wave device 12) behaving differently from a rigid film (e.g., metal electrodes 28) deposited thereon. The rigid film deposited on a surface of acoustic-wave device 12 moves synchronously with the surface as the surface oscillates in a shear mode of vibration characterized by an in-plane displacement (i.e., motion parallel to the surface of the piezoelectric material). This motion of the rigid film produces a change in a stored or kinetic energy of device 12 which decreases a resonant frequency of oscillation of device 12 in proportion to an areal mass density (i.e., density times thickness) of the deposited rigid film. Because moving the rigid film does not result in a dissipation of energy, however, there is no measurable change in the damping voltage.

On the other hand, a compliant film (e.g., paraffin) is generally viscoelastic (i.e., having both an elastic character and a viscous character) with a lower portion of the compliant film moving synchronously with the surface (exposed side 4 in FIG. 3) of crystal plate 26 on which it accumulates, and an upper portion of the compliant film that lags behind the motion of the surface. This lagging motion can produce a shear strain within the compliant film which can affect both an energy storage within the compliant film and an energy dissipation thereof. As the compliant film becomes thicker (e.g., due to an increased accumulation of the solidified constituents) the frequency of oscillation (or the shift thereof) which initially decreases due to an accumulation thereon can subsequently increase as the accumulation is further increased. Thus, depending on the application of the present invention, a combination of the frequency of oscillation (or the shift thereof) and the damping voltage or current (or the shift thereof) can be used for greater precision. The damping voltage is sensitive to both a change in the viscosity of the petroleum-based composition (e.g., due to precipitation of paraffins) and also to the accumulation of the paraffins on the exposed surface of crystal plate 26 of acoustic-wave device 12.

FIG. 3 shows an embodiment of the present invention suitable for analyzing petroleum-based composition 100 in a pipeline or storage tank. A similar arrangement can be used for attaching the acoustic-wave sensor apparatus 10 to a storage tank, wherein there may be no actively-controlled temperature cooling other than that due to ambient temperature changes. The present invention can be used in these and other cases to sense the onset of solidification of constituents due to ambient temperature changes or due to compositional changes of the constituents.

Acoustic-wave device 12 can be mounted within a housing with the both of the surfaces of crystal plate 26 (exposed side 4 and isolated side 6) parallel to the flow direction of composition 100, or flush-mounted with the pipeline tee so that only a single surface (e.g., either exposed side 4 or isolated side 6) thereof is exposed to the composition 100. By flush mounting crystal plate 26, the potential for crystal damage and for suspended solids interfering with the deposition monitoring is minimized. Crystal plate 26 can be surrounded by a diaphragm 260, or equivalent support structure, that supports crystal plate 26 within the pipeline. Diaphragm 260 can be bonded to crystal plate 26 with, for example, epoxy. Diaphragm 260 is preferably constructed of a resilient material such as buna-n rubber. Crystal plate 26 can be mounted with a backup ring 215 to prevent pressure bending of crystal plate 26 and minimize thermal gradients. Backup ring 215 can be constructed of rigid or semi-rigid material to prevent breakage of crystal plate 26. For example, backup ring 215 can be constructed from a high thermal conductivity material. Diaphragm 260 is pressure molded or bonded to outer pipe plug 205 and backup ring 215. The pipeline embodiment 200 is configured with outer pipe plug 205 to mate with the pipeline tee (not shown); this pipeline tee plug implementation allows the deposition monitor to be screwed into the pipeline tee for easy in-line application. Pipeline cap or inner plug 208 mates with outer plug 205 to form chamber 210 between inner plug 208 and crystal plate 26 and diaphragm 260. Inner plug 208 is preferably constructed of metal although other materials can be used depending upon the implementation. Insulation material 270 is provided between chamber 210 and inner plug 208 and outer plug 205 to prevent heat from transferring from external sources to chamber 210; insulation material 270 is not necessary in all applications. Thermal insulation of internal chamber 210 by insulation material 270 minimizes heating and/or cooling losses.

Pipeline embodiment 200 includes means within chamber 210 for ensuring electrical isolation of the two surfaces (exposed side 4 and isolated side 6) of crystal plate 26 to allow the deposition monitor to work in composition 100 that conducts electricity. In practice, electrical isolation means can be a fluid that does not conduct electricity and isolates exposed side 4 of crystal plate 26 from isolated side 6 of crystal plate 26, isolation means can be any incompressible material that is not electrically conductive. For example, the isolation means can be a silicon oil. Isolation means can be also be a compressible medium such as air, although other means would have to be incorporated into the structure to ensure that crystal plate 26 does not break due to pressure in chamber 210. Fluid-filled chamber 210 and flexible mounting diaphragm 260 cooperate to provide automatic pressure balancing across crystal plate 26.

The embodiment of FIG. 3 further includes an internal baffle screen 220 to disrupt or deflect compressional waves that can occur in fluid-filled chamber 210. Other means of disrupting or deflecting such compressional waves will become apparent to those skilled in the art. For example, a deflector can be mounted in a v-shaped fashion to accomplish the same purpose.

Means 230 for heating and cooling crystal plate 26 can include a commercially-available thermoelectric cooler or heater. The heat transfer coefficient from crystal plate 26 is constrained by the equation $h=Nu_D k/\delta$, where $Nu_D$ is the Nusselt number, k is thermal conductivity, and $\delta$ is the thickness of the boundary layer. In one embodiment, the Nusselt number, $Nu_D$, for the laminar layer on crystal plate 26 is approximately four, the thermal conductivity k is 0.0623 w/m° C. (water @ 25° C.). The boundary layer is assumed to be 0.1 to 0.01 of the pipe radius. Assuming a two-inch pipe radius results in the heat transfer coefficient of h equal to from about 0.5 to 5 w/° C. for the nominal one-inch diameter of the crystal.

A commercially-available FerroTech 6300/071/060 thermoelectric module (1.17" by 1.17"—diagonal 1.65") can transfer greater than 27 watts at a ΔT of 10° C. or less differential temperature (6 amps—10 volts applied power). Thus, a single stage of thermoelectric cooler 234 should be able to cool crystal plate 26 from about five to fifty C. Additional cooling/heating can be obtained by stacking thermoelectric coolers as necessary. By installing the deposition monitor with the crystal facing down, adverse effects of convection during cooling can be eliminated.

For a fluid compressibility of $10 \times 10^{-11}$ cm²/dynes ($6.8 \times 10^{-6}$ psi$^{-1}$), a pressure of 10,000 psi will cause a fractional compression of $6.8 \times 10^{-2}$ (in/in) or 0.034" for a ½" deep chamber 210. A 0.034" deflection of crystal plate 26 and backup ring 215 will not be excessive.

A thermoelectric feedthrough 232 is provided with apparatus 200 to provide a connection between temperature controller 234 and means 230. Thermoelectric feedthrough 232 is potted with high-pressure low-compressibility material. Temperature controller 234 monitors the ambient temperature conditions and controls the temperature of means 230. Electrical circuit 14 (described above with reference to FIG. 1) is electrically connected to crystal plate 26 through crystal feedthrough 280. Crystal feedthrough 280 is potted with high-pressure low-compressibility material. As shown in FIG. 3, crystal feedthrough 280 can also be electrically connected to temperature controller 234 to provide on-the-crystal temperature measurement to provide accurate crystal temperatures. As discussed above, electrical circuit 14 can be an oscillator circuit such as that described by Wessendorf (U.S. Pat. No. 5,416,448). The temperature of crystal plate 26 is controlled by circuitry 10 that senses the ambient temperature and crystal plate 26 temperature and adjusts the power to thermoelectric cooler 234 accordingly.

For a deposition point determination, crystal plate 26 is generally heated initially to a temperature at which any solidified constituents are dissolved (e.g., about 15° C. or more above an estimated cloud-point temperature for the petroleum-based composition 100); and then crystal plate 26 is cooled at a predetermined rate generally about 0.2°–2° C./minute while measuring output signal 16 from acoustic-wave device 12 and the temperature as measured by temperature controller 234. The temperature range for operation of apparatus 200 is from greater than 85° C. to about 0° C. or less, limited only by the cooling capacity of Peltier elements 510. 85° C. is generally adequate to melt even the highest molecular weight paraffins.

When paraffin crystallizes, the change that takes place is basically a physical change. The paraffin molecules exist in solution before the deposition and the molecular structure of these molecules is not changed by the deposition process. The process is reversible unless something else changes, e.g., something that acts like "cloud seeds" for the paraffin crystals is changed by the deposition process. In general, paraffin deposition occurs as a result of lowering the temperature decreasing the solubility of the paraffin molecules. One exception is the deposition of paraffin as the result of evaporation of the light ends of crude oil. Even in this case, the paraffin should go back into solution as the temperature rises. Thus, if the deposition monitor detects deposition as a result of cooling crystal plate 26, a simple test as to whether the deposit is paraffin, is to raise the temperature of crystal plate 26 and determine whether the deposit goes away. As the temperature is raised, the paraffin can go back into solution.

Asphaltenes exist before deposition not as molecules in solution, but as large amorphous particles in colloidal suspension. Each particle has its own unique composition containing a variety of different chemical bonds and structures. Normally these particles are held in suspension by an outer "sheath" that is soluble in crude oil. Associated with deposition of asphaltenes is usually a chemical change in the outer "sheath" such that inner insoluble material (the asphaltene itself) is now in contact with the crude oil or "walls of the pipe," etc. The effectiveness of this "sheath" can be disrupted by an increase in temperature. In either case, the deposition process is generally not reversible and frequently results in the agglomeration of individual particles into larger particles. Asphaltene deposits become softer upon heating, but generally do not melt, whereas paraffins melt. If the crystal surface is heated sufficiently above the cloud-point temperature, then this also, can be used to distinguish between the paraffins and asphaltenes.

Figure 5:
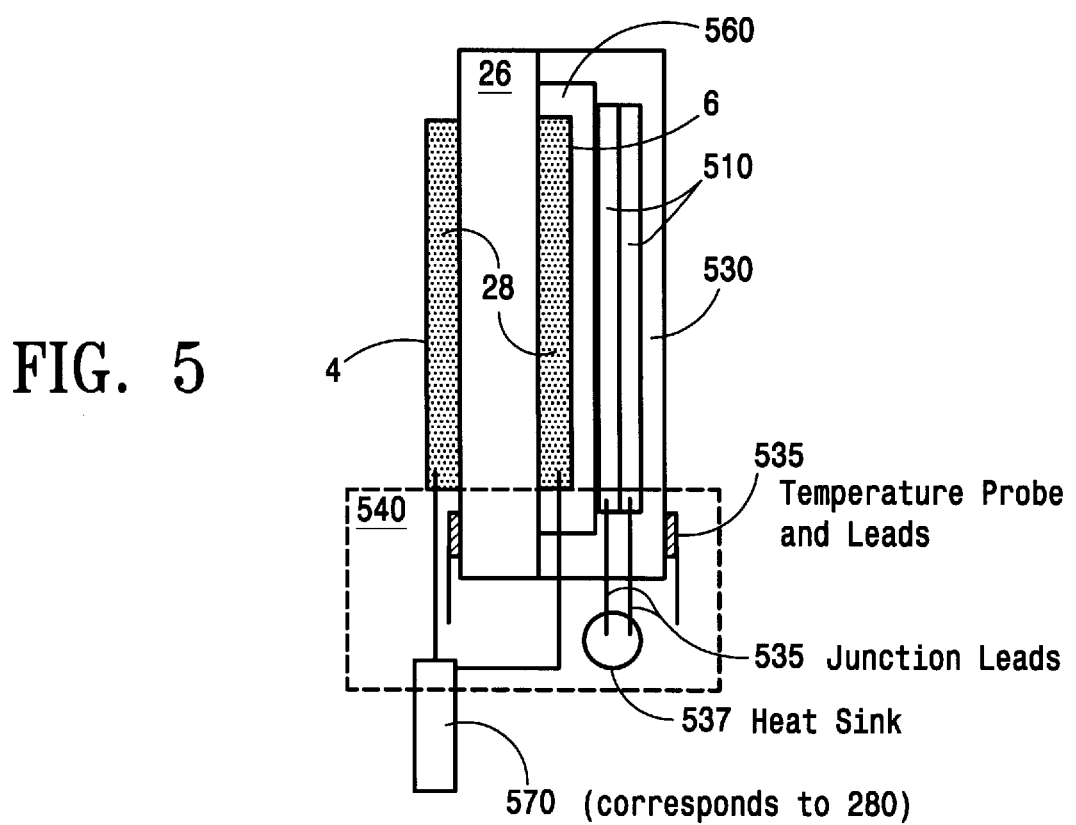
FIG. 5 shows a side view of a third embodiment of the present invention using a Peltier junction.

Referring to FIG. 5, a third embodiment of the present invention includes placing a Peltier junction on crystal plate 26 using the junction to cool and heat crystal plate 26 as discussed below. Yet another embodiment includes selective coatings on crystal plate 26 so that deposition of different crystal species can be distinguished. Still another embodiment includes placing different chemicals in composition 100 so that the deposition monitor can be used to test the effectiveness of the chemicals in controlling deposition. A further embodiment includes placing different coatings on crystal plate 26 to test the effectiveness of coatings (e.g., in pipelines) in retarding deposition. By analyzing the signal of the TSM response, it is possible to distinguish between viscoelastic and rigid deposits.

Any means known to the art can be used for varying the temperature of crystal plate 26 relative to the temperature of composition 100, including cooling crystal plate 26 with a coolant (e.g., liquid or gaseous nitrogen, ammonia or a fluorinated hydrocarbon, etc.), or heating crystal plate 26 with an electric heater. A heater (not shown) or the like can be provided proximate to acoustic-wave device 12 for periodically removing the accumulation of solidified constituents from acoustic-wave device 12. Such a heater could be provided, for example, as a thin-film or thick-film resistance element on a common wafer or plate 26 with acoustic-wave device 12, as a heating element in thermal contact therewith, or a portion of composition 100 in contact with acoustic-wave device 12.

However, as discussed above, and referring to the third embodiment 500 of FIG. 5, the temperature variation means can include one or more Peltier junction elements 510 (i.e., thermoelectric elements) in contact with crystal plate 26 and electrically activated through electrodes 28 to control and vary the temperature of crystal plate 26. By using Peltier junction elements 510, there is no need for diaphragm 260 or chamber 210 as discussed above. Peltier junction elements 510 can be attached to crystal plate 26 for effective heating and cooling thereof depending upon a direction of flow of an electrical current provided to Peltier elements 510. Peltier elements 510 can be electrically activated by signal connections 570 (which correspond to 280 in FIG. 3). Peltier elements 510 can be controlled by a temperature controller (not shown) through temperature probes and leads 535 providing the electrical current in response to a feedback signal provided by a temperature readout, or a separate temperature sensor attached to the acoustic-wave device 12. The temperature controller allows the temperature of crystal plate 26 to be maintained at a particular temperature above or below the deposition point. Alternately, temperature controller 234 can be used in combination with Peltier elements 510 for varying the temperature of crystal plate 26 (either upward, downward, or both) over a predetermined temperature range that includes the deposition-point temperature. The temperature-variation step can be initiated, for example, in response to a signal provided by signal processing unit 24 to temperature controller 234, or by temperature controller 234 itself upon manual triggering. An optional electrically-insulating, thermally-conducting layer 560 can be provided around crystal plate 26 adjacent isolated surface 6. Additionally, a thermal insulation material 530 is provided around Peltier elements 510. Peltier junction leads 520 connect Peltier elements 510 to a heat sink Peltier junction 537, which serves to remove heat from crystal plate 26 to the heat sink 537. Mounting block 540 is provided to support crystal plate 26 and its associated components in this third embodiment.

Although, controlling or varying the temperature of composition 100 being analyzed is not necessary for the present invention, those skilled in the art will recognize that for certain applications, independently controlling both the temperature of the crystal and the temperature of the fluid being analyzed can enhance the utility of the present invention.

A determination of characteristics of petroleum-based compositions including the deposition point, is important for evaluating or designing recovery, handling, transportation and refining systems for petroleum-based compositions. Furthermore, these characteristics determine, at least in part, a temperature range for usage each petroleum-based composition and thus a market value for each petroleum-based composition. During recovery, transport, storage and refining of crude oil, any exposure to equipment, pipelines or wellbores at temperatures below the deposition-point temperature can lead to a solidification of constituents (e.g., paraffin or petroleum wax) from the crude oil and a deposition of the solidified constituents on cooler surfaces of the equipment, pipelines or wellbores. The solidified constituents can limit system capacity and require provision for removal of the solidified constituents by heat, chemicals, or mechanical scraping. Furthermore, dehydration of a waxy crude below its deposition point is generally not efficient because some of the precipitated wax concentrates at an oil/water interface and builds a rag layer that does not allow movement of water, thereby reducing an efficiency for dehydration which can only be corrected by an increased temperature.

Acoustic-wave sensor apparatus 10 according to the embodiment shown in FIG. 3 can be used for sensing changes in fluid properties within a pipeline or storage tank that occur at the deposition point (e.g., formation of a slurry of solidified constituents which increases the viscosity of composition 100) or to sense deposition of constituents on an inner surface of the pipeline or storage tank.

By monitoring output signal 16 from acoustic-wave device 12 as a function of time to measure an accumulation of solidified constituents from composition 100 on one or more surfaces of acoustic-wave device 12, apparatus 200 can provide an indication of deposition and deposition rate of the constituents on an inner surface of the pipeline (or alternately an inner surface of a storage tank). Such solidification can occur when the temperature of the crystal surface is reduced below the deposition-point temperature, or when the deposition-point temperature is raised above the temperature of the petroleum-based composition due to an excess of paraffin or wax in composition 100 (e.g., during crude oil recovery). This type of monitoring can be performed without temperature controller 234, although the provision of temperature controller 234 is generally to be preferred because it provides additional information about the temperature of crystal plate 26 (e.g., for quantifying the deposition-point temperature).

The present invention can also be operatively connected to means for maintaining petroleum-based composition 100 above or below a predetermined deposition point; or above or below a predetermined product of density times viscosity. As an example, acoustic-wave sensor apparatus 10 could be located on a sea-floor well head to detect when crude oil being recovered is below a deposition point, with the information provided by apparatus 10 being used to signal an alarm, or to initiate or increase a chemical injection or heat injection into the wellbore to raise the crude oil above the deposition point. Such chemical injection could be in the form of any additive known to the art, including a solvent for dissolving at least in part the solidified constituents, or a surfactant or dispersant for limiting or preventing deposition of particles. This would improve crude oil recovery by reducing production costs and also the cost of controlling paraffin deposition.

Similar improvements are expected for refining petroleum-based constituents (or during use thereof). For example, the apparatus and method of the present invention could be used within a refinery, with acoustic-wave sensor apparatus 10 signaling an alarm when a petroleum-based constituent within a pipeline or storage tank reaches the deposition point. Alternately, apparatus 10 could be used in a closed-loop feedback mode (e.g., with an output from signal processing unit 24) to maintain a petroleum-based composition above a predetermined deposition point by chemical injection, or by heat injection, or by filtering (including centrifuging) the petroleum-based composition to remove at least a portion of any solidified constituents therein before deposition, or by blending the petroleum-based composition with an additive as described heretofore or with another batch of a hydrocarbon composition having a smaller quantity of constituents that solidify (e.g., blending different batches of petroleum-based compositions to provide a predetermined deposition-point temperature for a product). In this way, the present invention can provide precise measurements to allow a closer regulation of refining or processing to maximize yield and reduce a cost for refining without sacrificing quality.

A deposition monitor and method can have a significant impact on many applications. The present invention is expected to find use in a wide variety of cases where deposition point is of interest. While the present invention has been introduced with respect to a petroleum-based composition for convenience, it should be understood that the present invention can be used to monitor the deposition point of any fluid composition that has a temperature-dependent deposition point (e.g., salts in water). Thus, the present invention has applications in a wide variety of processing industries including food, plastics, waste, etc. Examples include, but are not limited to, the pipeline industry, all types of chemical processing and manufacture where in-line sensors would allow smart, real-time process control. The ability to monitor deposition could have a significant economic impact on the oil and other industries by allowing the treatments to inhibit or remove deposition to be selectively applied. Until the present invention, there was no simple in-line real-time sensor that can monitor deposition of paraffins.

Other variations and modifications of the present invention will be apparent to those of skill in the art, and it is the intent of the appended claims that such variations and modifications be covered. The particular values and configurations discussed above can be varied and are cited merely to illustrate a particular embodiment of the present invention and are not intended to limit the scope of the invention. For example, although acoustic-wave device 12 is shown flush mounted in FIG. 3, in other embodiments of the present invention, acoustic-wave device 12 can be mounted in a different configuration as long as one side of crystal plate 26 remains in contact with composition 100 being analyzed while the other side of crystal plate 26 is heated/cooled. Furthermore, in some embodiments of the present invention, temperature sensor 18 (e.g., a platinum resistance temperature sensor (RTD)) can be formed alongside acoustic-wave device 12 on the piezoelectric plate or wafer. It is contemplated that the use of the present invention can involve components having different characteristics as long as the principle, the presentation of a real-time sensor for monitoring deposition by active heating/cooling of crystal plate 26, is followed. It is intended that the scope of the present invention be defined by the claims appended hereto.

We claim:

1. An apparatus for analyzing a normally-liquid petroleum-based composition having constituents in a solution which solidify and deposit on a surface when such surface is below a deposition-point temperature of the composition, the apparatus comprising:

acoustic-wave sensing means having an exposed surface, the exposed surface being in contact with the petroleum-based composition for detecting the presence of constituents deposited on the exposed surface and for generating an output signal in response to the deposition thereon; and temperature varying means, thermally connected to the acoustic-wave sensing means, for causing the temperature of the acoustic-wave sensing means to drop below the deposition-point temperature of the liquid petroleum-based composition.

2. The apparatus of claim 1, wherein the constituents are paraffins.

3. The apparatus of claim 1, further comprising a temperature sensing means in thermal contact with the acoustic-wave sensing means for measuring the temperature of the acoustic-wave sensing means.

4. The apparatus of claim 1, further including a support for holding the acoustic-wave sensing means and making electrical contacts thereto.

5. The apparatus of claim 1, further comprising electrical circuit means connected to the acoustic-wave sensing means for activating the acoustic-wave sensing means and for generating the output signal therefrom.

6. The apparatus of claim 5, wherein the output signal indicates a parameter of the acoustic-wave sensing means selected from the group consisting of a frequency of oscillation, a shift in the frequency of oscillation, a damping voltage, a shift in the damping voltage, a damping current, and combinations thereof.

7. The apparatus of claim 5, wherein the output signal is responsive to an accumulation of constituents on the exposed surface.

8. The apparatus of claim 5, wherein the temperature varying means comprises temperature cooling means, for causing the temperature of the acoustic-wave sensing means to drop below the deposition-point temperature of the liquid petroleum-based composition.

9. The apparatus of claim 8, wherein the temperature varying means further comprises temperature heating means, for causing the temperature of the acoustic-wave sensing means to rise above the deposition-point temperature of the liquid petroleum-based composition.

10. The apparatus of claim 9, wherein a change to a predetermined temperature of the acoustic-wave sensing means resets the acoustic-wave sensing means to a known condition.

11. The apparatus of claim 9, wherein a rise in temperature of the exposed surface allows constituents that dissolve to be differentiated from constituents that do not dissolve as the temperature of the exposed surface rises.

12. The apparatus of claim 5, wherein the temperature varying means varies the temperature of the exposed surface over a predetermined range of temperatures.

13. The apparatus of claim 12, wherein the temperature varying means is a thermoelectric cooler.

14. The apparatus of claim 12, wherein the temperature varying means is a Peltier junction.

15. The apparatus of claim 13, wherein said acoustic-wave sensing means comprises a crystal, the crystal having the exposed surface and an isolated surface opposite the exposed surface, and comprises a housing adapted for mounting in a pipeline and for containing the crystal, and wherein the exposed surface of the crystal is mounted flush with respect to a fluid flow direction of the composition and is mounted within the housing in the pipeline.

16. The apparatus of claim 15, wherein the housing comprises a pipeline tee having a section that is perpendicular to the fluid flow direction, the pipeline tee having side walls and a cap located opposite the isolated surface, and the temperature varying means being located adjacent the cap and within the housing.

17. The apparatus of claim 16, further comprising electrical isolation means located within the chamber for ensuring electrical isolation of the exposed surface from the isolated surface.

18. The apparatus of claim 17, wherein the electrical isolation means is a material that does not conduct electricity.

19. The apparatus of claim 18, wherein the material is incompressible.

20. The apparatus of claim 16, further comprising insulation material provided along the side walls of the pipeline tee to prevent heating and cooling losses due to sources external to the chamber (210).

21. The apparatus of claim 17, further comprising an internal baffle screen for disrupting compressional waves that can be present in the composition in the pipeline.

22. The apparatus of claim 17, further comprising temperature controlling means, connected to the temperature varying means, for controlling the temperature of the temperature varying means.

23. The apparatus of claim 22, further comprising a connection between the temperature controlling means and the electrical circuit means such that the electrical circuit means changes the temperature of the acoustic-wave sensing means in response to temperature controlling means.

24. The apparatus of claim 12, wherein the temperature varying means is a Peltier junction formed on the acoustic-wave sensing means for heating and cooling the exposed surface.

25. The apparatus of claim 1, wherein the acoustic-wave sensing means is selected from the group consisting of thickness-shear-mode devices, surface-acoustic-wave devices, acoustic-plate-mode devices, and flexural-plate-wave devices.

26. The apparatus of claim 1, wherein the output signal is operatively connected to controlling means for maintaining the petroleum-based composition above the deposition-point temperature.

27. An apparatus for analyzing the deposition rate of a normally-liquid petroleum-based composition having constituents in a solution which solidify and deposit on a surface where such surface is below a deposition-point temperature of the composition, the apparatus comprising:

acoustic-wave sensing means having an exposed surface and an isolated surface, the exposed surface being in contact with the petroleum-based composition for detecting the presence of constituents deposited on the exposed surface and for generating an output signal in response to the deposition thereon;

temperature varying means for causing the temperature of the exposed surface to drop below the deposition-point temperature of the constituents in the composition; and means for monitoring the rate of deposition of the constituents as a function of temperature of the exposed surface.

28. A method for analyzing a normally-liquid petroleum-based composition having constituents in a solution which solidify and deposit upon a surface when such surface is cooled below a deposition-point temperature of the composition, the method comprising the steps of:

contacting the petroleum-based composition with at least one surface of an acoustic-wave device;

actively cooling the one surface of the acoustic-wave device over a predetermined range of temperatures including the deposition-point temperature of the petroleum-based composition; activating the acoustic-wave device with an electrical circuit and measuring at least one parameter thereof which varies in response to deposition of the constituents; and measuring and recording the temperature of the one surface of the acoustic-wave device to determine if the constituents have deposited on the one surface.

29. The method of claim 28, wherein the step for activating the acoustic-wave device comprises applying a radio-frequency (rf) electrical signal to the device and exciting an acoustic vibration mode therein.

30. The method of claim 29, wherein the radio-frequency (rf) electrical signal is applied to the acoustic-wave device by connecting the device to the electrical circuit and with an electrical circuit coupling designed such that said acoustic-wave device forms a frequency-control element of the electrical circuit.

31. The method of claim 28 wherein the step for measuring the parameter of the acoustic-wave device includes measuring a change of the parameter from an unperturbed value thereof in the absence of the deposited constituents.

32. The method of claim 28 wherein the measured parameter of the acoustic-wave device is selected from the group consisting of a frequency of oscillation, a shift in the frequency of oscillation, a damping voltage, a shift in the damping voltage, a damping current, or a combination thereof.

33. The method of claim 28, further comprising the step of raising the temperature of the one surface of the acoustic-wave device to a predetermined temperature to reset the acoustic-wave device to a known condition by removing any deposited constituents therefrom.

34. The method of claim 28, further comprising the step of providing means for monitoring the rate of deposition of the constituents as a function of temperature.

* * * * *